United States Patent
Christiansen, II et al.

(10) Patent No.: US 7,657,101 B2
(45) Date of Patent: Feb. 2, 2010

(54) DEVICES AND METHODS FOR IDENTIFYING AND MONITORING CHANGES OF A SUSPECT AREA ON A PATIENT

(75) Inventors: William T Christiansen, II, Sammamish, WA (US); Eric R Steinmetzer, Sammamish, WA (US); James E Torelli, Bothell, WA (US)

(73) Assignee: DermaSpect, LLC, Sammamish, WA (US)

( * ) Notice: Subject to any disclaimer, the term of this patent is extended or adjusted under 35 U.S.C. 154(b) by 270 days.

(21) Appl. No.: 11/336,649

(22) Filed: Jan. 19, 2006

(65) Prior Publication Data
US 2006/0210132 A1   Sep. 21, 2006

Related U.S. Application Data

(60) Provisional application No. 60/645,538, filed on Jan. 19, 2005.

(51) Int. Cl.
*G06K 9/68* (2006.01)
(52) U.S. Cl. .................... 382/218; 382/118; 382/133; 600/306
(58) Field of Classification Search ........... 382/128, 382/132, 218, 133, 118; 600/306
See application file for complete search history.

(56) References Cited

U.S. PATENT DOCUMENTS

| | | | | |
|---|---|---|---|---|
| 5,627,907 A | * | 5/1997 | Gur et al. ................. 382/132 |
| 5,673,300 A | * | 9/1997 | Reckwerdt et al. ........... 378/65 |
| 5,910,972 A | * | 6/1999 | Ohkubo et al. .............. 378/54 |
| 5,974,165 A | * | 10/1999 | Giger et al. ................. 382/132 |
| 6,208,749 B1 | * | 3/2001 | Gutkowicz-Krusin et al. ................. 382/128 |
| 6,215,893 B1 | * | 4/2001 | Leshem et al. ............. 382/128 |
| 6,266,453 B1 | * | 7/2001 | Hibbard et al. ............ 382/294 |
| 6,359,513 B1 | * | 3/2002 | Kuo et al. ................. 330/276 |
| 6,396,270 B1 | * | 5/2002 | Smith ..................... 324/309 |
| 6,427,022 B1 | * | 7/2002 | Craine et al. ............. 382/128 |
| 6,594,388 B1 | * | 7/2003 | Gindele et al. ............ 382/167 |
| 6,603,552 B1 | * | 8/2003 | Cline et al. ............... 356/417 |
| 6,648,820 B1 |   | 11/2003 | Sarel ..................... 600/300 |
| 6,941,323 B1 | * | 9/2005 | Galperin ................ 707/104.1 |
| 7,128,894 B1 | * | 10/2006 | Tannous et al. ............ 424/9.1 |
| 7,136,191 B2 | * | 11/2006 | Kaltenbach et al. .......... 358/1.9 |
| 7,162,063 B1 | * | 1/2007 | Craine et al. ............. 382/128 |

(Continued)

FOREIGN PATENT DOCUMENTS

WO    WO 97/47235    12/1997

(Continued)

*Primary Examiner*—Gregory M Desire
(74) *Attorney, Agent, or Firm*—Seed IP Law Group PLLC

(57) ABSTRACT

A device for acquiring first and subsequent images of a suspect area on a patient and methods for monitoring or detecting changes of the suspect area over time and providing notification when the changes exceed a threshold. The device may be an imaging device, such as a digital camera, possibly augmented with physical or optical devices for arranging the orientation and/or distance of the imaging device with respect to the suspect area. In addition, methods for identifying, relocating, acquiring a first and/or subsequent image of the suspect area, and performing a comparative analysis of respective images are also described. Results of the comparative analysis can be used to notify and/or assist a medical professional in treating or counseling the patient.

19 Claims, 13 Drawing Sheets

U.S. PATENT DOCUMENTS

| | | | |
|---|---|---|---|
| 7,298,881 B2* | 11/2007 | Giger et al. | 382/128 |
| 2003/0004405 A1* | 1/2003 | Townsend et al. | 600/407 |
| 2003/0006770 A1* | 1/2003 | Smith | 324/309 |
| 2003/0036751 A1* | 2/2003 | Anderson et al. | 606/9 |
| 2004/0201694 A1* | 10/2004 | Gartstein et al. | 348/207.99 |
| 2004/0264749 A1* | 12/2004 | Skladnev et al. | 382/128 |
| 2005/0033142 A1* | 2/2005 | Madden et al. | 600/407 |
| 2005/0259281 A1* | 11/2005 | Boust | 358/1.9 |
| 2006/0036156 A1* | 2/2006 | Lachaine et al. | 600/411 |
| 2006/0092315 A1* | 5/2006 | Payonk et al. | 348/370 |
| 2006/0098876 A1* | 5/2006 | Buscema | 382/195 |
| 2006/0210132 A1* | 9/2006 | Christiansen et al. | 382/128 |
| 2006/0269125 A1* | 11/2006 | Kalevo et al. | 382/162 |

FOREIGN PATENT DOCUMENTS

WO WO 2004/095372 A1 11/2004

* cited by examiner

DEVICES AND METHODS FOR IDENTIFYING AND MONITORING CHANGES OF A SUSPECT AREA ON A PATIENT

BACKGROUND OF THE INVENTION

1. Field of the Invention

This disclosure relates to devices and methods, which can be used alone or in combination, to identify and monitor changes of a suspect area on a patient, for example dermatological changes.

2. Description of the Related Art

There are many reasons why a medical professional, patient, or both would want to monitor changes on an exterior or internal surface of a patient. For a suspect area, especially one that may indicate some form of skin cancer, it is important to detect and treat the area in its early stages. One type of skin cancer is known as melanoma, which is a malignant cancer of the pigment cells (melanocytes). Other forms of skin cancer also exist and are known as basal and squamous cell cancers, which are tumors of unpigmented cells (keratinocytes) of the skin.

Melanocytes occur at various depths within the epidermal (upper) and dermal (lower) layers of skin. Melanocytes are normally distributed in the layers of the skin and produce pigment in response to being subjected to ultraviolet light (e.g., sunlight). Aggregated melanocytes are termed naevus cells and can be indicative of a melanoma. Because a melanoma may appear as a mole, medical professionals typically attempt to ascertain whether the suspicious area is changing over time. Identifying changes early typically results in a rapid diagnosis, which in turn often leads to rapid and highly effective treatments that can greatly increase the patient's survival rate and in most cases, complete recovery.

Historically, the standard of care for screening or monitoring melanoma is a visual inspection or visual comparison of photographs by a medical professional. These visual inspections or comparisons are subjective and do not enable the medical professional to detect small or subtle changes in a suspect area. Changes in the perimeter, depth, shape, and even color of a melanoma can be subtle for a time and then progress rapidly. Moreover, changes in the color or perimeter, for example, of a melanoma are not easily discernable to the human eye so these changes may go unnoticed for a long period of time.

In U.S. Pat. No. 6,427,022, issued to Craine et al., a skin lesion is monitored by obtaining a series of digital baseline images over time and comparing these images. The method of comparison taught in Craine et al. is that the baseline image is compared visually by the viewer with a subsequently obtained image by alternately displaying the respective images, in a blinking fashion. The blinking action is created by quickly alternating the images with respect to one another on a display monitor to enable the viewer to detect changes in the skin lesion.

Even though the standards of care discussed above may involve images, each standard of care suffers from the subjectivity and uncertainty associated with the medical professional trying to ascertain changes in a suspicious area by visual comparison. The visual comparison methods are subjective and less accurate for a number of reasons. For instance, the medical professional may be inexperienced, may have been distracted during the examination, or may have selected the wrong location on the patient's body during a follow-up examination.

Therefore, a more effective, less subjective, and low-cost approach for at least monitoring changes in a suspect area is desirable.

SUMMARY OF THE INVENTION

It should be understood that one aspect of the present invention is the comparison of a plurality (e.g., at least two) images taken at different times utilizing a computer based algorithm that can overlay two images and either transform the images to fit over each other or do a best fit analysis thereby denoting or calling out one or more of any color, perimeter, or depth changes. In one embodiment the analysis can include transforming the images to match color, contrast, angle, focus (sharpness), brightness, and subsequently comparing the multiple images with each other. Changes between the images may be called out in a variety of ways. Such embodiments include text reports, highlight or color coding the image itself, etc.

In another aspect a device or apparatus is contemplated that comprises a digital image capture device and a distance-measuring device. In certain embodiments the distance measuring device measures the distance between the suspect area and the image capture device and provides a read-out or a tone to signify the optimal distance. Further, embodiments include the use of a reference such as a strip of adhesive affixed to the surface or attached the device that provide contrast, color, sharpness, and/or depth references. Such an embodiment could include an adhesive strip having a color palette (e.g., one or more colors), gray scale, distance references (hash marks) or depth references.

In certain embodiments of the invention distance measurements can be done by a sonic device, laser or any other means of measuring distance.

In one particular embodiment an enclosed tube or housing is affixed to the image device and positioned over the suspect area. In one embodiment of such a device the housing or enclosure is essentially light free and may contain its own light source internally to provide consistent lighting of the suspect area. In a specific embodiment the enclosure is a tube of a fixed length have LEDs or fiber optics positioned inside. One end of such an enclosure may be fitted to the image capturing device and the other fitted over the suspect area.

In one aspect, an apparatus to acquire an image of a suspect area on a patient comprises an imaging device; and a separation tool having a first end connected with a first section, at least a portion of the first end formed to contact the patient, the first section having an attachment portion to receive the imaging device, the first section formed to maintain the imaging device at a substantially fixed distance from the suspect area.

In another aspect, an imaging assembly to image a suspect area on a patient comprises an imaging device and at least one sensor to indicate an orientation and/or distance of the imaging device relative to a first location.

In another aspect, an imaging assembly to image a suspect area on a patient comprises a housing; an imaging device located within the housing; and at least one sensor to indicate an orientation of the housing relative to a first location.

In yet another aspect, a method of acquiring an image of a suspect area includes identifying the suspect area; positioning a patient with the suspect area in approximately a first position; identifying a reference item located on the patient; determining a position of the suspect area in relationship to the reference item; aligning an imaging device to acquire the image of the suspect area; and acquiring the image after aligning the image device.

In yet another aspect, a method of comparing at least two images, each image capturing a suspect area includes identifying a reference item in the at least two images; measuring an attribute of the reference item in a first image; transforming a second image based on the measured attribute of the reference item in the first image, wherein a reference item in the second image is transformed to correspond with an orientation and size of the reference item in the first image; measuring an attribute of the suspect areas in both images; and comparing the respective measured attributes of the respective suspect areas. Such reference items can be points either away from the suspect area or within the suspect area. Further, the measured attribute can be color, distance between at least two points, total perimeter, distance between multiple points etc.

In one aspect the method of comparing two images comprises receiving at least two images digitally into a computer system, performing a fitting analysis on the at least two images to obtain an overlay and providing an output noting any differences between the at least two images.

In yet another aspect, a method of acquiring an image of a suspect area includes identifying the suspect area; positioning a patient with the suspect area in approximately a first position; aligning an imaging device to acquire an image of the suspect area; and acquiring the image after aligning the image device.

In still yet another aspect, a method of comparing at least two images of a suspect area on a patient includes providing at least two digital images of the suspect area; digitally overlaying the at least two images; performing a best-fit transformation of one image to encourage the one image to approximately correspond to at least one detected attribute of the other acquired image; comparing the at least two images to determine whether a difference exists between an aspect of the one image when compared with the same aspect of the other image.

In an even further aspect the present invention can be used in the context of full-body imaging wherein one or more digital or other image capture device or devices are placed around the patient and the full-body is imaged either in a piece by piece manner or in its entirety. These images can then be compared by transformation or best-fit analysis and analyzed for any changes by a computer algorithm.

BRIEF DESCRIPTION OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

DETAILED DESCRIPTION

Figure 1A:
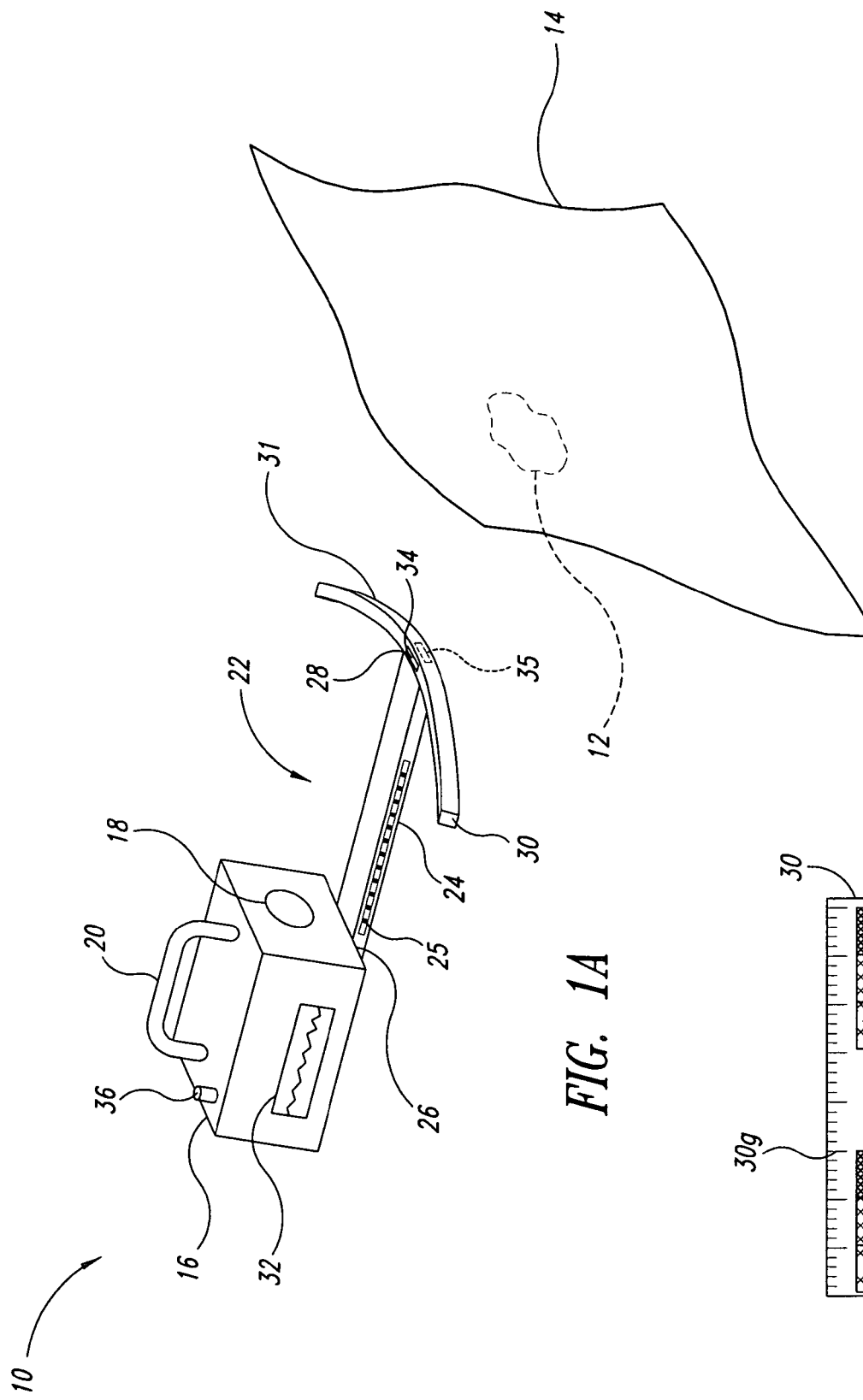
FIG. 1A is a front, left isometric view of an imaging device according to one illustrated embodiment positioned with respect to a portion of skin.

In the following description, certain specific details are set forth in order to provide a thorough understanding of various embodiments of the disclosed subject matter. However, one skilled in the art will understand that the embodiments may be practiced without these details. In other instances, well-known structures associated with imaging systems, computing systems and processors, and various techniques for manipulating and evaluating digital image data have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Unless the context requires otherwise, throughout the specification and claims that follow, the term "patient" refers primarily to warm blooded mammals and is not limited to human beings, but could include animals such as dogs, cats, horses, cows, pigs, higher and lower primates, etc.

The headings provided herein are for convenience only and do not interpret the scope or meaning of the claimed invention.

The embodiments disclosed herein are generally directed to acquiring images of a suspect area located on a patient, comparing the acquired images to one another; and evaluating the compared images to determine if some amount of change from one image to a subsequent image warrants a more detailed examination by a medical care professional. The embodiments disclose a number of different devices and methods for achieving such results.

The surface of interest can be either internal or external to the patient. In one instance, the surface of interest is the patient's exposed skin that is monitored for the detection or growth of skin cancer. In another instance, the surface of interest can be the patient's mucous membranes, interior body surfaces related to reproductive and/or digestive systems of the patient, ocular surfaces, or any other accessible surface on a patient. For purposes of this description, the surface of interest will be exemplified as an area on the patient's skin, referred to as a suspect area. However, this exemplification is not meant to limit or otherwise narrow the scope of the description, the claims, or any specific embodiment depicted herein.

The suspect area referred to herein can be the site of a suspected melanoma or mole (e.g., melanin containing areas to be monitored), but can also be any other suspect area on a patient that needs to be monitored. Thus, it is within the scope of this disclosure that the suspect area can be located in a variety of places on a patient, for example the patient's mucous membranes, surfaces of interior body cavities related to reproductive and/or digestive systems, ocular surfaces, or any other interior or exterior surface on a patient where monitoring is desired. In the exemplary embodiment used for discussion purposes, the suspect area can be a dermal feature, such a type of skin cancer, a skin lesion, a skin rash, a burn or scar, an infected or inflamed area, a wound, or some other skin anomaly that may or may not be capable of growth, reduction or other change. For example, one embodiment may monitor a healing rate (i.e., recession) of a burn or scar when certain medications, lotions, or creams are applied to the skin. A further embodiment envisions utilizing such technology to monitor the effectiveness of a drug or nutriceutical, such as those that heal the skin. Another embodiment may monitor a patient's scalp for hair loss and/or growth. In addition, the embodiments disclosed herein may be used in a number of settings, such as a home setting, a clinical setting, a laboratory or research setting, a regulatory compliance setting, or any combination of the above.

Devices and Systems to Acquire an Image of a Suspect Area

FIGS. 1A-3 show three different embodiments of a device to acquire an image of a suspect area. Each of the devices differs in its degree of complexity, accuracy, and cost. It is contemplated that many, if not all, of the features or aspects of one device can be incorporated into the other devices.

FIG. 1A shows a first imaging device 10 for imaging a suspect area 12 on skin 14 according to the illustrated embodiment. The first imaging device 10 includes a housing 16 and a lens 18 to receive and direct light to imaging components (not shown) located within the housing 16. By locating the imaging components in the housing 16, damage and/or exposure of the imaging components may be prevented. The housing 16 can have a handle 20 to permit the housing 16 to be lifted, moved, positioned, or otherwise manipulated. Additionally or alternatively, the handle 20 and/or other portions of the housing 16 can be configured with support locations so that the imaging device 10 can be secured to a tripod, for example.

The imaging components may take the form of a camera or an optical scanner operable to capture images of the suspect area 12. In one embodiment, the camera may advantageously take the form of a digital image capture device such as a CCD or CMOS type camera. A CCD camera may consist of one-dimensional or two-dimensional arrays of charge coupled devices ("CCD") and suitable optics, such as optical lenses, for focusing an image on the CCD array. CCD arrays can capture whole images at a time, or can be electronically controlled to successively sample (e.g., pixel-by-pixel, row-by-row, or column-by-column) the information on a region of the skin 14 (i.e., electronically scan). Alternatively, the imaging components can take the form of a CMOS imager capable of capturing one-dimensional or two-dimensional arrays similar to that of a CCD reader.

Employing a digital image capture device advantageously provides the image in a form suitable for use with a data processing system such as a computing system. Alternatively, the camera may take the form of a non-digital image capture device, such as a film camera. Such embodiments may employ image scanners, or other devices to digitize the images captured on film. The imaging device 10 may advantageously take the form of a still image capture device. Alternatively, the imaging device 10 may take the form of a motion picture capture device such as a movie camera or video camera. Such embodiments may include a frame grabber or other device to capture single images.

The imaging device 10 may rely on ambient light, or may include one or more light sources, such as light emitting diodes ("LEDs") or incandescent lights, which may be manually or automatically controlled.

Figure 1B:
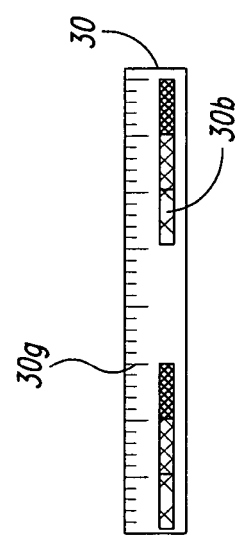
FIG. 1B is a side view of a portion of a guide of the imaging device of FIG. 1A having measurement markers and a palette according to one illustrated embodiment.

A guide 22 is attachable to the housing 16 of the imaging device 10. The guide 22 is configured so that the housing 16 can be placed at a desired distance away from the skin 14 along a Z-axis, perpendicular to an X-Y plane when an image is acquired. In the illustrated embodiment, the guide 22 includes an extension member 24 having a first end 26 that is coupled to the housing 16 of the imaging device 10. A second end 28 is coupled to a contact member 30. The contact member 30 can include a number of features to enhance the control and/or optimization of the imaging device 10. For example as illustrated in FIG. 1B, the contact member 30 of the guide 22 can include measurement markings 30a, similar to those of a ruler, and/or contrast markings 30b, which can represent a color or grayscale palette.

In one embodiment, the extension member 24 includes adjustable, complementary sliding members with gradations 25 to allow the housing 16 to be placed at a desired distance from the suspect area 12. In another embodiment, the extension member 24 is formed to be non-adjustable, thus the housing 16 is set at a fixed length from the contact member 30. The contact member 30 may be shaped (e.g., arc-shaped) to provide an unobstructed line of sight between the imaging device 10 and the suspect area 12. As will be discussed in more detail below, it may be desirable that the contact member 30 be shaped such that at least a portion of the contact member 30 can be captured in the acquired image. A skin contact region 31 of the contact member 30 can be padded to provide a more comfortable interaction with the patient. One skilled in the art will understand and appreciate that the first end 26 can be coupled to the housing 16 by any number of mechanical methods, for example fasteners, clips, VELCRO®, adhesive bonding, tie down straps, or some other structure that substantially keeps the housing 16 attached to the extension member 24.

In the illustrated embodiment, the imaging device 10 can include at least one sensor 32 for determining an orientation of the device 10. One advantage of determining the orientation of the device 10 is to provide for repetitive and consistent images in an X-Y plane, especially if the images are acquired at different times. For example, if a second image is being acquired of the suspect area 12, but the imaging device 10 is tilted or rotated at too much of an angle, the second image may be too distorted or misaligned to digitally process or compare to a previously acquired image.

A variety of sensors 32 can be used to indicate the orientation of the imaging device 10. In the illustrated embodiments, the sensor 32 is a fluid level encompassed in the housing 16 and visible by a user of the imaging device 10. The sensor 32 may also be integrated with the guide 22. The fluid level sensor 32 generally indicates whether the imaging device 10 is tilted relative to the ground. Additionally or alternatively, a gyroscope, which is sometimes referred to as a tilt sensor, can be used to determine an acceleration of the imaging device 10 about at least one axis.

In addition to or instead of sensing the orientation of the imaging device 10, other sensors 34 can be used to determine the proximity of the imaging device 10 in relation to the skin 14 of the patient. In one embodiment, a pressure sensor 34 is located in the contact member 30 to sense the pressure exerted on the contact member 30 as it is positioned against the skin 14 of the patient. By sensing the pressure that the imaging device 10 is pressed against the skin 14, the imaging device 10 can be repetitively and accurately repositioned relative to the suspect area 12 from one image to the next. Additionally or alternatively, a proximity sensor 35 can be used to detect when the contact member 30 is at a desired distance from the patient, to include when the contact member 30 barely makes contact with the patient.

Each of the sensors 32, 34, and/or 35, described above, as well as equivalent sensors, can be electronically coupled with the imaging device 10 to provide an indication that the imaging device 10 is at the desired orientation or distance. For example, the imaging device 10 can have an indicator 36 that sends a visual and/or audio signal to indicate when the imaging device 10 is at the desired orientation, distance, and/or when an amount of pressure is present between the contact member 30 and the patient. A signal from the indicator 36 would indicate that the image could be acquired at that moment in time. Likewise, the sensors 32, 34, and/or 35 can also be electronically coupled with a processor (not shown) to computationally update the orientation and/or proximity to the patient of the imaging device 10. In one embodiment, the processed information can be displayed on a screen (not shown) located on the housing 16.

Figure 2A:
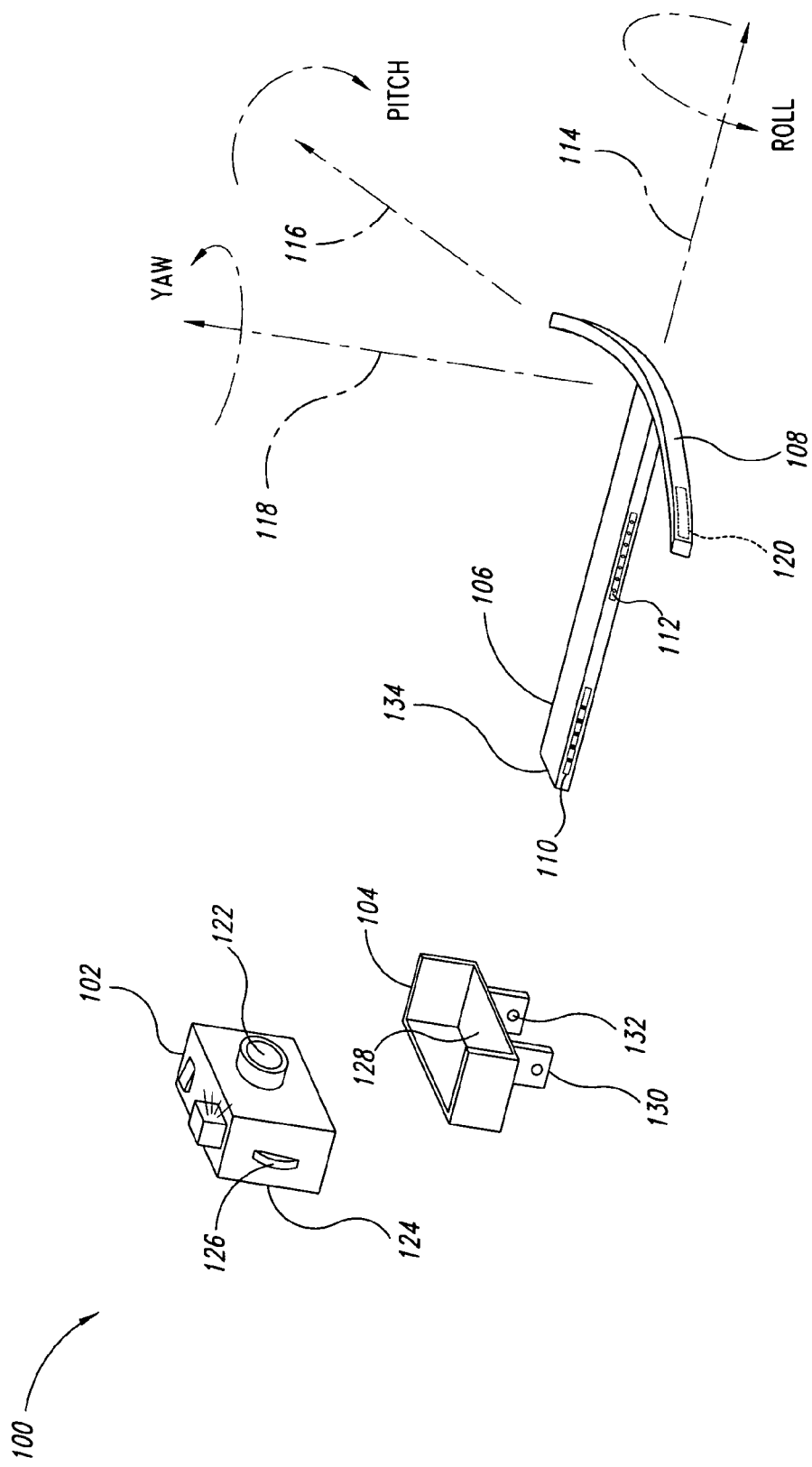
FIG. 2A is a partially exploded, front, left, isometric view of an imaging device according to another illustrated embodiment.

FIG. 2A shows a second imaging device 100 that includes a camera 102 and a member 104 for receiving and coupling the camera 102 to an extension member 106. Similar to the extension member discussed above, the extension member 106 includes a contact member 108. In addition, the extension member 106 further includes detents 110 sized and configured to complementarily receive the member 104, a sensor 112 to indicate the orientation of the extension member 106 about a Roll axis 114, a Pitch axis 116, and/or a Yaw axis 118, and a color palette 120 that can be used to provide color and/or contrast balancing once the image is acquired and archived. Color and/or contrast balancing are described in more detail below.

The camera 102 can be a digital camera as described in the previous embodiment or a film camera that includes at least a lens 122, a camera body 124, an image trigger 126. The camera can capture images on photographic film (not shown), which can be standard photographic film that is purchased in a store and is configured to be chemically processed in a photo lab after it has been exposed to light. Alternatively, the photographic film may be specialized film, such as film that is sensitive to the non-visible portions of the electromagnetic spectrum, such as infrared or ultraviolet sensitive films.

In the illustrated embodiment, the member 104 includes a compartment 128 that is sized to receive the camera 102 and a pair of flanges 130 formed to couple to the extension member 106. A front portion 128 of the compartment 128 does not obstruct the lens 122 of the camera 102 when the camera 102 is seated in the compartment 128. The camera 102 can be secured to the member 104 by virtue of the compartment 128 being sized to provide a tight or snug fit for the camera body 124. Alternatively, hook and loop fastener pads, commonly available under the trademark VELCRO®, can be provided to keep the camera 102 relatively secure in the compartment 128. One skilled in the art will appreciate and understand that securing the camera 102 in the compartment 128 can be accomplished in a variety of known ways.

The flanges 130 are further formed to complementarily engage the detents 110 provided on the extension member 106. In the illustrated embodiment, the flanges 130 include rounded, depressible buttons 132. Sliding a first end 134 of the extension member 106 in between the flanges 130 and permitting the buttons 132 to click into the detents 110, so that the contact member 108 is at a desired distance from the camera 102, accomplishes the assembly of the member 104 with the extension member 106.

Figure 2B:
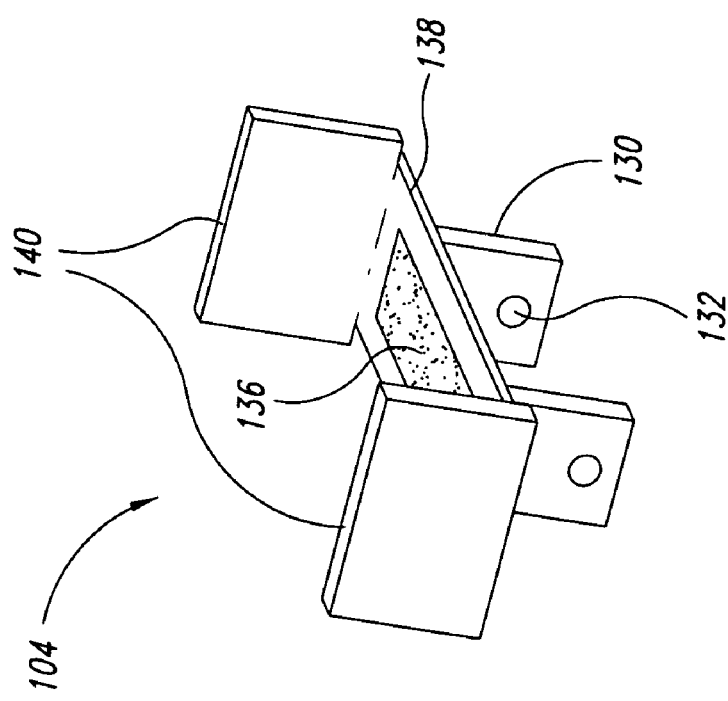
FIG. 2B is a front, left isometric view of an intermediate bracket according to one illustrated embodiment.

FIG. 2B shows a different embodiment of a member 104 without a compartment. Instead, a bonding strip 136 is provided on a base 138 of the member 104. Each side 140, extending from the base 138 can be biasly resilient to form a snug fit with the camera 102. The bonding strip 136 can be a pad of hook and loop fastener, a tacky substance, or other equivalent object or substance.

Figure 3:
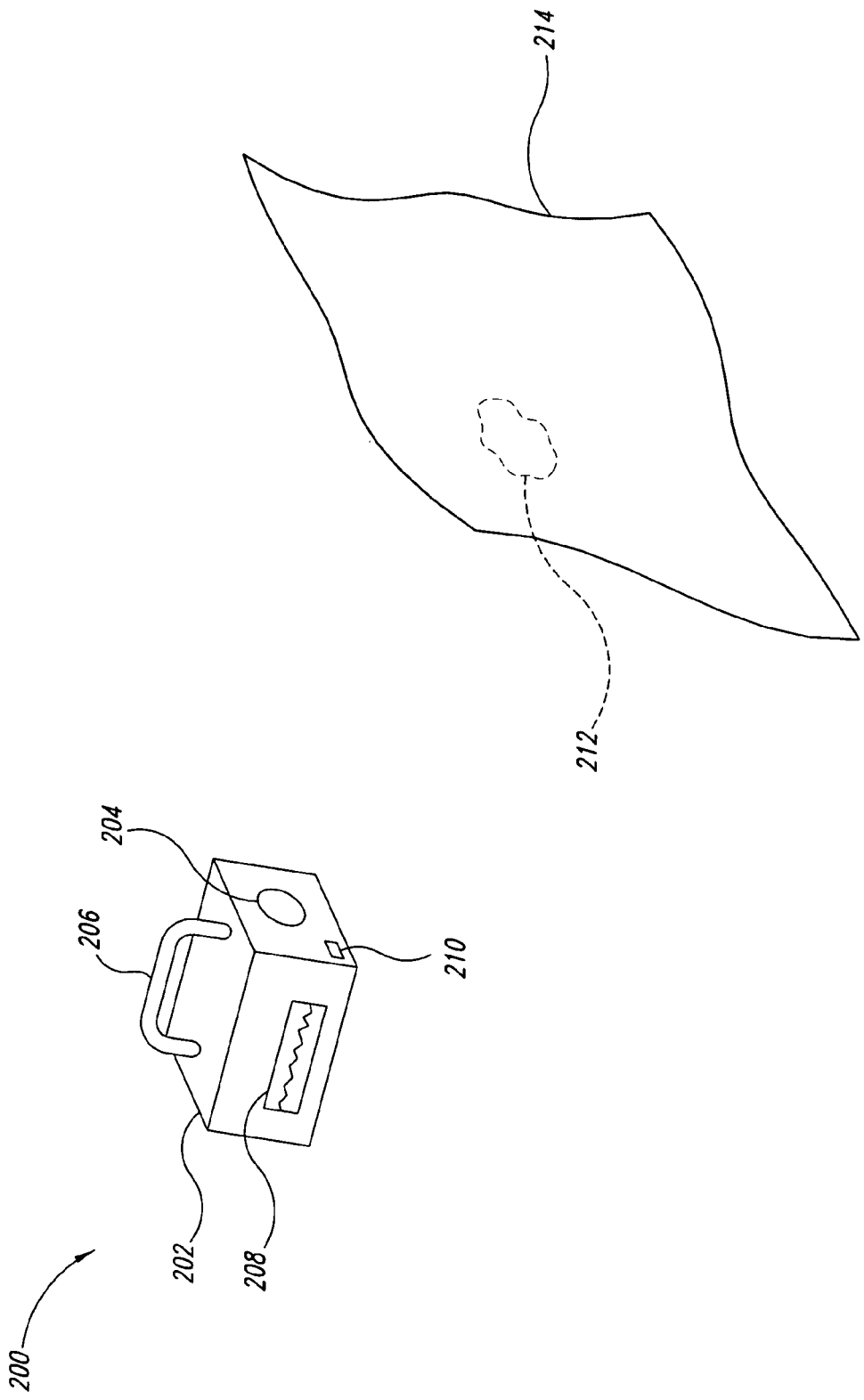
FIG. 3 is a front, left, isometric view of an imaging device according to another illustrated embodiment.

FIG. 3 shows an automated imaging device 200 according to another embodiment. Many of the aspects of the imaging device 200 are similar to the aspects described in the previous embodiments, for example a housing 202, an imager 204, a handle 206, and a sensor 208. One difference between the imaging device 200 and the previously described devices 10, 100 is that the present embodiment does not employ an extension member. In lieu of the extension member, a second sensor or range finder 210 is used to indicate the distance between the imaging device 204 and a suspect area 212.

In one embodiment, the range finder 210 is a laser triangulation sensor that provides non-contact linear displacement measurements of the suspect area 212 on the skin 214. A laser beam (e.g., from a semiconductor laser) is reflected off the skin 214. A returning beam is received and focused onto a CCD sensing array (not shown) of the imager 204. The CCD array detects the peak value of the light and determines the distance of the skin 214 based on the position of the beam spot. The range finder 210 produces an analog voltage that is proportional to the distance of the skin 214 from the range finder 210.

As an alternative to the above embodiment, the range finder 210 can be a laser interferometer, an ultrasonic sensor, or an equivalent sensor to measure the linear distance of the dermal suspect 212 to the range finder 210. Laser interferometers use the length of a wave of light as the unit for measuring position and consist of three basic components, a laser that supplies a monochromatic light beam, optics that direct the beam and generate an interference pattern, and electronics which detect and count the light and dark interference fringes and output the distance information. Ultrasonic sensors offer another means to make non-contact distance measurements. An ultrasonic sensor works by measuring the time it takes a sound wave to propagate from the range finder 210, to an object and back to the range finder 210. In the illustrated embodiment, the skin 214 would reflect the ultrasonic waves generated by a transmitter and then a receiver would detect the returning waves. The elapsed time from initial transmission to reception of the returning waves is used to determine the distance to the skin 214.

The monochromatic light used to illuminate at least the suspect area 212 during imaging can have a wavelength outside of the visible portion of the light spectrum. For example, the monochromatic light can be in a frequency range of ultraviolet light, infrared light, or some other non-visible range along the light spectrum.

In yet another embodiment, the imaging device 200 is a camera. Again, the imaging device 200 may advantageously take the form of a still image capture device, a motion picture capture device such as a movie camera or video camera. In the present embodiment, the alignment of the imaging device 200 is accomplished manually without the aid of an extension member or sensor. The acquired images are compared in a best-fit analysis. The best-fit analysis includes digitizing the images and matching key points or parameters of a first image onto similar key points or parameters of a second image. For example, the perimeter or border of the first image can be matched to the perimeter or border of the second image. It is appreciated that in one embodiment the first image and the second image are of the same suspect area and the best-fit analysis is employed to detect changes, if any, of the suspect area over time without respect to using other reference points and/or markers to align and/or orient the imaging device 200 relative to the suspect area. The analysis software can transform, rotate, and otherwise manipulate at least one of the images until enough similarities are found between the two compared images to verify that both images are of the same suspect area or are possibly not of the same suspect area. The best-fit analysis is described in more detail below in the discussion on image comparison.

Devices and Systems to Acquire Images of Larger Surfaces

In one embodiment, a system is capable of contemporaneously acquiring images over a variety of locations on a patient. The system can capture images over a larger surface area or can take multiple images over a larger area where the multiple images can be digitally overlaid and matched to form a large image.

Methods of Identifying and Re-Locating a Suspect Area

Figure 4:
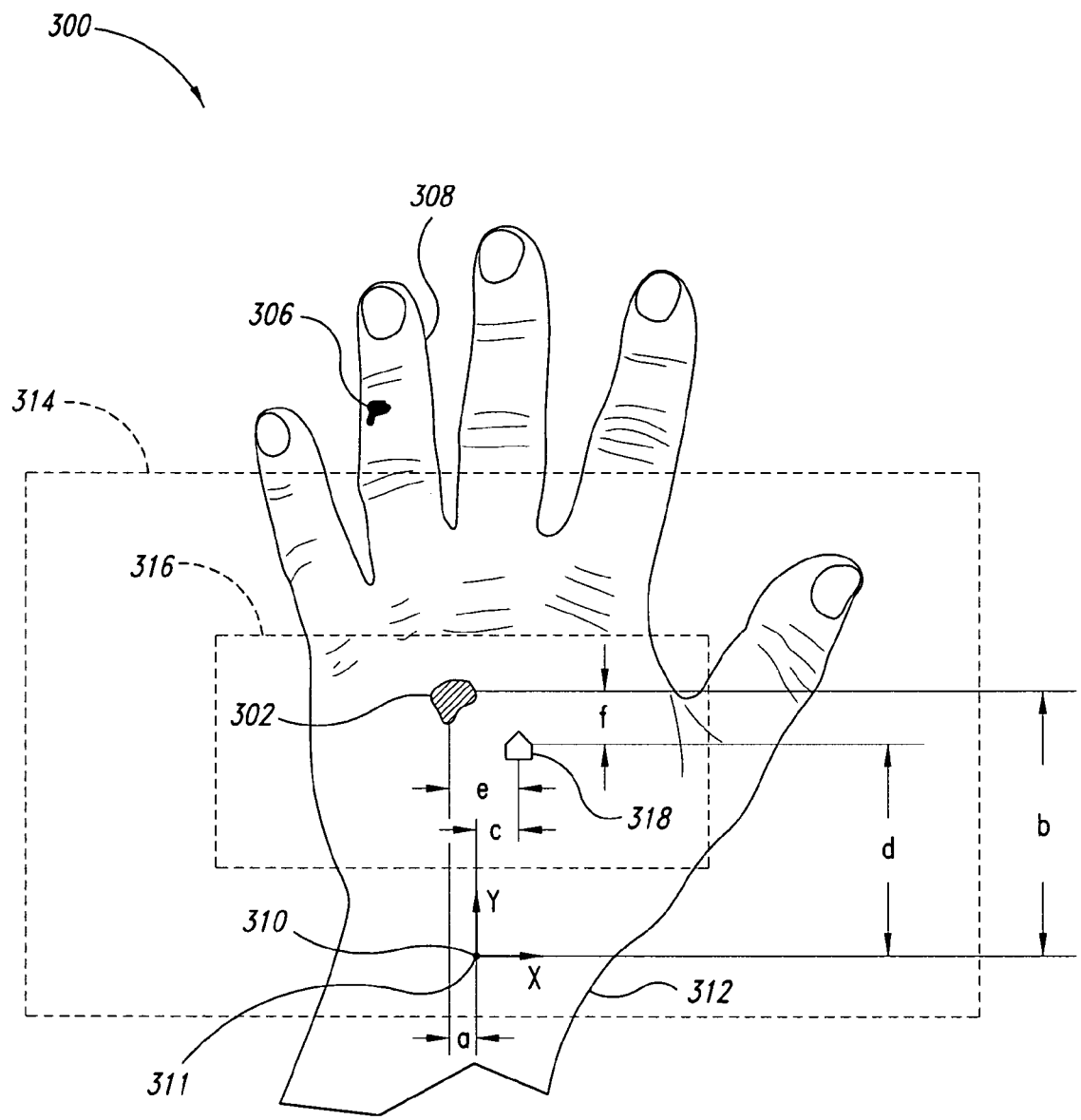
FIG. 4 is an elevational view of a hand having several reference points for locating a suspect area according to one illustrated embodiment.

FIG. 4 shows a patient's hand 300 according to one embodiment. By way of example, a suspect area 302 (e.g., a grouping of melanoma cells) appears on a backside surface 304 of the patient's hand 300. Two spots are identifiable on the backside surface 304, a first spot 306 (e.g., a scar) is located on the ring finger 308 and a second spot 310 (e.g., a freckle) is located on the wrist 312 of the patient's hand 300. The spots 306, 310, respectively, can be freckles, birthmarks, borders of a limb, or some other equivalent feature or landmark that is not susceptible to substantial changes in shape, size, and/or location with respect to its present location on the patient. Further, the spot 306 or 310 may be naturally occurring, such as a freckle, or the spot 306 or 310 may be a portion of a scar, a tattoo, or some other feature that is not susceptible to substantial changes in shape, size, and/or location with respect its present location on the patient.

One advantage of locating at least one of the spots 306 or 310 on the patient is to use one of the spots 306 or 310 as a reference object 311. The reference object 311, which is equivalent to spot 310 in the illustrated embodiment, provides a starting point from which other key measurements can be taken, as explained in the method below. However, it is appreciated that a reference object 311 is not always necessary when the suspect area can be easily relocated. For example, a group of melanoma cells that is easily and routinely detectable on a patient could be imaged and re-imaged, especially when the images are compared using a best-fit analysis.

The selection of the spots 306, 310 is generally left to the discretion of the medical professional, and it is contemplated that the medical professional will select the spot 310 that is the most stable or less susceptible to change over time. Optionally, the imaging software may also select the spots 306, 310. Although the first spot 306 may have a stable configuration, such as the scar, the location of the spot 306 on the ring finger 308 makes it less attractive as an reference object 311 because the ring finger 308 is easily moveable in relation to the hand 300, which can add error in repetitive measurements taken with respect to the spot 306 on the ring finger 308. In contrast, the second spot 310, shown on the wrist 312, has a more fixed relationship with respect to the suspect area 302 and thus may be a better reference object 311 from which to measure and document the location of the suspect area 302.

It is also advantageous if the reference object 311 or at least a reference marker 318 is located proximate to the suspect area 302 so that the reference object 311 or reference marker 318 can be captured in an image of the suspect area 302. In accordance with the embodiments herein and described in more detail below, it is desirable to manipulate an image by matching or overlaying either the reference objects 311 or reference markers 318 that appear in different images, taken at different times. In the illustrated embodiment, the reference marker 318 has a defined size and shape and can be placed quite near the suspect area 302. The advantage, however, of locating the reference object 311 remains unchanged because the placement of the reference marker 318 on the patient is made relative to the location of the reference object 311 on the patient.

Methods of Acquiring a First Image of a Suspect Area

Figure 5A:
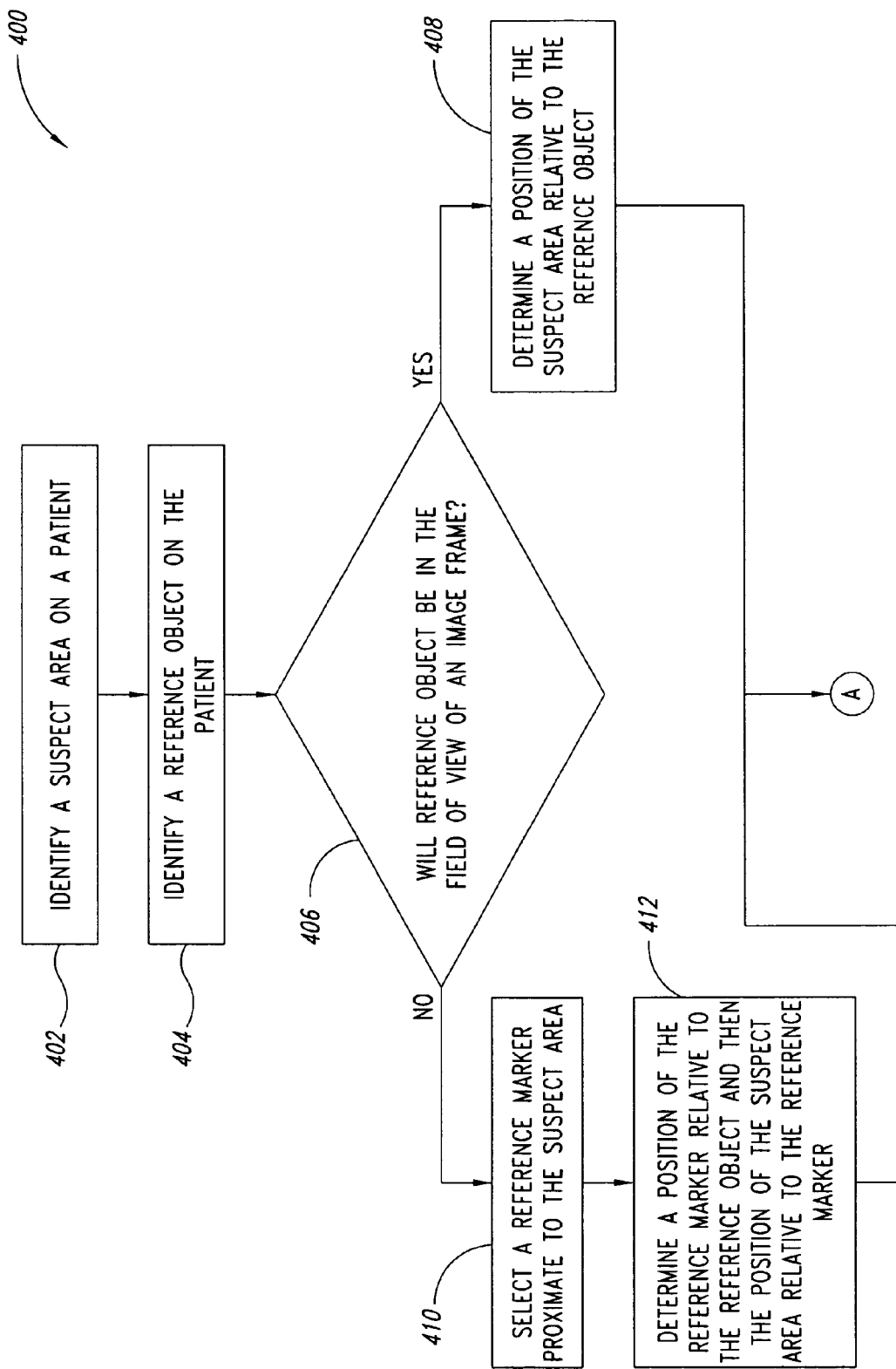
FIG. 5A is a flowchart of a method of identifying a suspect area according to one illustrated embodiment.
Figure 5B:
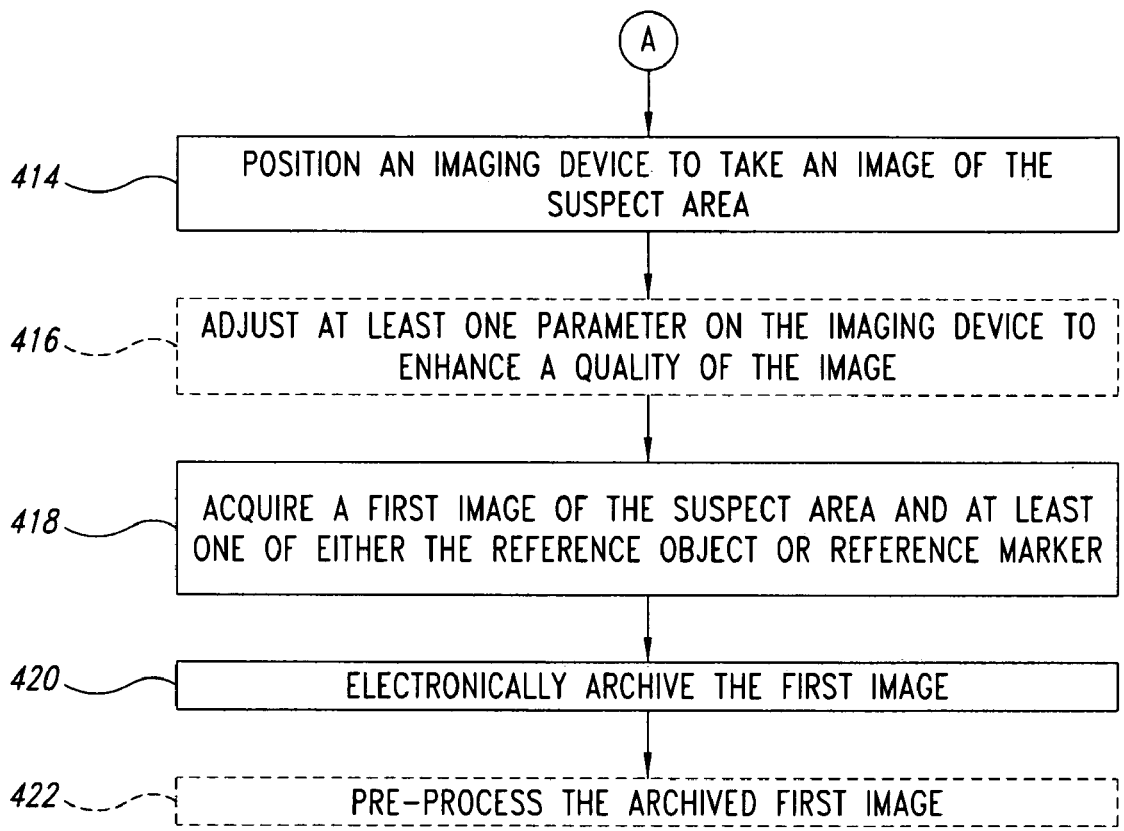
FIG. 5B is a continuation of the flowchart of FIG. 5A.

FIG. 5 is a flowchart illustrating a method 400 to identify and take an image of a suspect area 302 on a patient. For clarity and ease of explanation, the method 400 is described in reference to FIG. 4. One aspect of locating the suspect area 302 is to accurately identify, map, and document the reference object 311, the marker 318, if needed, and the suspect area 302 for image comparison purposes as described in greater detail below.

FIG. 5 shows that the method 400 commences at 402 where the suspect area is identified on the patient. A medical professional, the patient, the computing system, or some other entity may identify the suspect area. Identifying the suspect area most often will be done visually, but it is understood that other approaches may be used, such as the sense of touch.

At 404, a reference object is identified on the patient. At 406, the medical professional determines whether the reference object will be within a first field-of-view or first frame 314 (FIG. 4) of an imaging device. Recall, it is desirable to have the reference object 311 within the first frame 314 of because multiple images of the suspect area 302 will be compared to one another. In one embodiment, the first frame 314 is sized to provide an amount of resolution of the suspect area 302 that will be adequate for detailed image processing and evaluation.

If the reference object 311 is advantageously within the first frame 314 of the imaging device, then at 408, a position of the suspect area 302 is determined relative to the reference object 311. In one embodiment, a Cartesian coordinate system (X, Y) having perpendicular axes, is used to determine the position of the suspect area 302 relative to the reference object 311. In another embodiment, a spherical coordinate system (r, θ) is used. By way of the exemplary embodiment illustrated in FIG. 4, which employs the Cartesian coordinate system, the reference object 311 is assigned coordinates "0, 0" and the suspect area 302, as measured from the reference object 311, is determined to have coordinates of (a, b) at a point on the suspect area 302 that represents an approximate center point of the suspect area 302. If a smaller image frame 316 (FIG. 4) is necessary, for example to get an image with higher resolution, and the reference object 311 is located outside of the smaller image frame 316, then at 410, the reference marker 318 (FIG. 4) is placed in proximity to the suspect area 302. At 412, a position of the reference marker 318 is determined relative to the reference object 311, for example the position of the reference marker 318 is determined to have coordinates (c, d). Next, the position of the suspect area 302 is determined relative to the reference marker 318 and, by way of example, has coordinates (e, f).

In one embodiment, the reference marker 318 is a pen mark on the patient. In another embodiment, the reference marker 318 is a small patch or sticker backed with an adhesive. The shape of the patch is customized so that the reference marker 318 can be placed in a desired orientation during successive examinations of the patient. In the illustrated embodiment of FIG. 4, the reference marker 318 includes a pointed region that points towards the finger tips and parallel sides that substantially align with the sides of the patient's arm. One skilled in the art will understand and appreciate that the reference marker 311 can have a variety of shapes, sizes, colors, contrast features, textures, and can even have features, like a center dot, to identify an exact starting point for measurements. Additionally or alternatively, human-readable and/or machine-readable indicia can be encoded on the reference marker 318.

It should be understood that in certain aspects of the invention no reference object is utilized per se, and the computer algorithm performs best fit on two images using only the suspect area or multiple points within the picture frame to make a transformation or best fit analysis. While user applied reference markers or the use of anatomical features as reference points are useful and may lead to higher quality results in certain scenarios, they are by no means required and thus should be considered optional embodiments. In addition, when utilizing such analysis in certain embodiments a computer algorithm can take points on the perimeter of the lesion or suspect area of a first image and perform multiple measurements between any two points or more and compare such measurements with a second image. The first and second image may be resized, skewed, color balanced and/or brightness changed to assist in attempting to fit one image to the other. When measurements between points in the first image and measurements between points in the second image are substantially the same the images can be considered compared and any deviations outside the error for such comparisons can be noted as a possible change for the user or medical professional to review.

The coordinates of the reference object 311, the reference marker 318, if needed, and the suspect area 302 can be recorded and/or documented on paper or via and electronic medium, for example entering the data into a computer. In addition, descriptions of these features can also be recorded and/or documented. It is understood that the recordation and/or documentation can be accomplished in a number of known ways, which may be through manual, automatic, paper, or paperless means. At 414, an imaging device 10, 100, 200 is positioned to take an image of the suspect area 302. Because the images will be digitally processed, it is desirable to position the imaging device 10, 100, 200 in a repeatable manner with respect to the suspect area 302. Depending on the type of method used to compare images and the quality of the images, it may desirable that the distance of the imaging device 10, 100, 200 from and the angle of the imaging device 10, 100, 200 with respect to the suspect area 302 is kept substantially constant from one image to the next. However, it is appreciated and understood that the distance and angle of the imaging device 10, 100, 200 with respect to the suspect area 302 can vary by a significant amount from one image to the next and the analysis/comparison software can best-fit analysis to substantially match and align respective images. In addition, it may also be desirable to maintain constant lighting, at least within the frame of the image, in order to more easily detect color changes and/or shape changes of the suspect area 302 when the images are electronically processed and compared.

In another embodiment, the imaging device 10, 100, 200 can include a stereo camera to add depth perception to the resulting image. Stereo cameras that are placed at a constant distance from each other could provide two images, one from each camera, of the suspect area 302. When the images are compared against each other, the depth and/or texture of the suspect area 302 can be determined.

Optionally, at 416, a parameter on the imaging device 10, 100, 200 may be adjusted to enhance a quality of the image. For example, light filters or color filters can be coupled with the imaging device 10, 100, 200 as a way to control the light within the frame of the image. Additionally or alternatively, the imaging device 10, 100, 200 can be focused to obtain a desired resolution, thus increasing or decreasing the frame size of the image to be acquired.

At 418, a first image is acquired that captures the suspect area 302 alone or the suspect area with one of either the reference object 311 or the reference marker 318. At 420, the first image is electronically archived. During the archiving process, the first image can be given an identifier such as a file name, label, number, date stamp, or some other association that makes it easy to re-locate the first image in a database. The electronic format of the first image can be archived as any number of common graphics formats such as *.jpg, *.tif, *.bmp, *.gif, or another equivalent format that is readable by a standard computer system.

Optionally, at 422, the first image may be preprocessed. Pre-processing the first image may include, but is not limited to, identifying the reference object 311 and/or reference marker 318 in the image; detecting, mapping, and computing the border of the object 311 and/or marker 318; detecting, mapping, and computing the border of the suspect area 302; and/or overlaying a reference grid 608 onto the image as shown in FIG. 6, according to one illustrated, exemplary embodiment.

Figure 6:
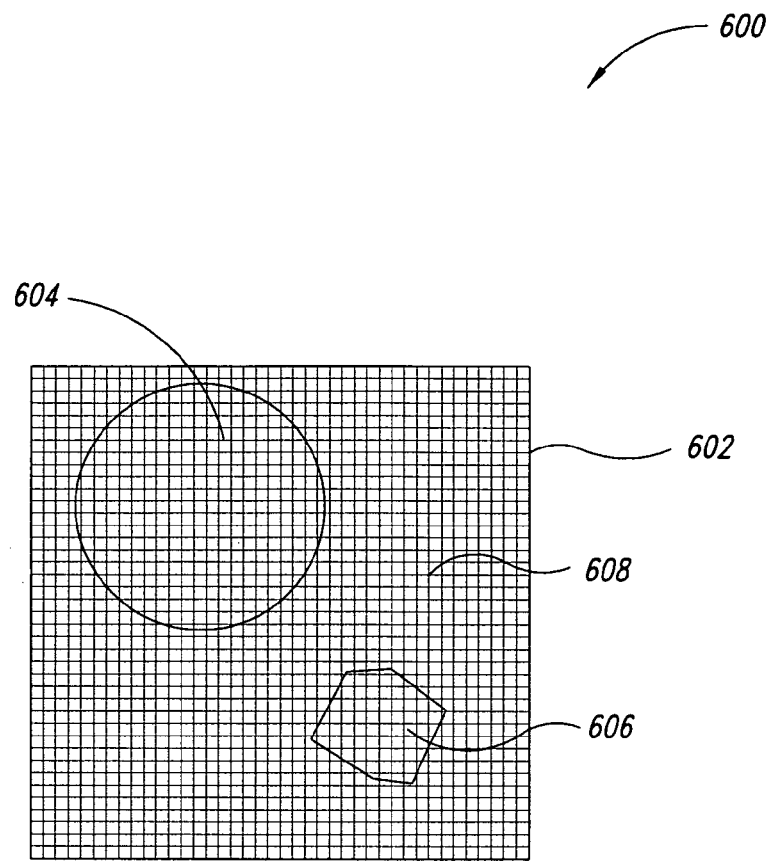
FIG. 6 is a top plan view of an image after the image has been pre-processed according to one illustrated embodiment.

FIG. 6 shows an image 600 having an image frame 602. Captured within the image frame 602 is an image 604 (i.e., an image of the suspect area 302) and a reference image 606 (i.e., an image of either one of the reference object 311 or the reference marker 318) located nearby or within image 604. The reference grid 608 overlies the image 604 and the reference image 606. One advantage of including the reference grid 608 is that the grid 608 can be printed with the image 600. This allows the medical professional to more easily visually examine the image 604 to identify obvious changes. Another advantage of the reference grid 608 is that it allows the medical professional to more accurately identify, describe, and even communicate respective changes of the suspect area 302 by referring to various quadrants or blocks of the reference grid, which can be colored or coded to indicate regions where substantial change has occurred.

Methods of Acquiring a Subsequent Image of a Suspect Area

Figure 7:
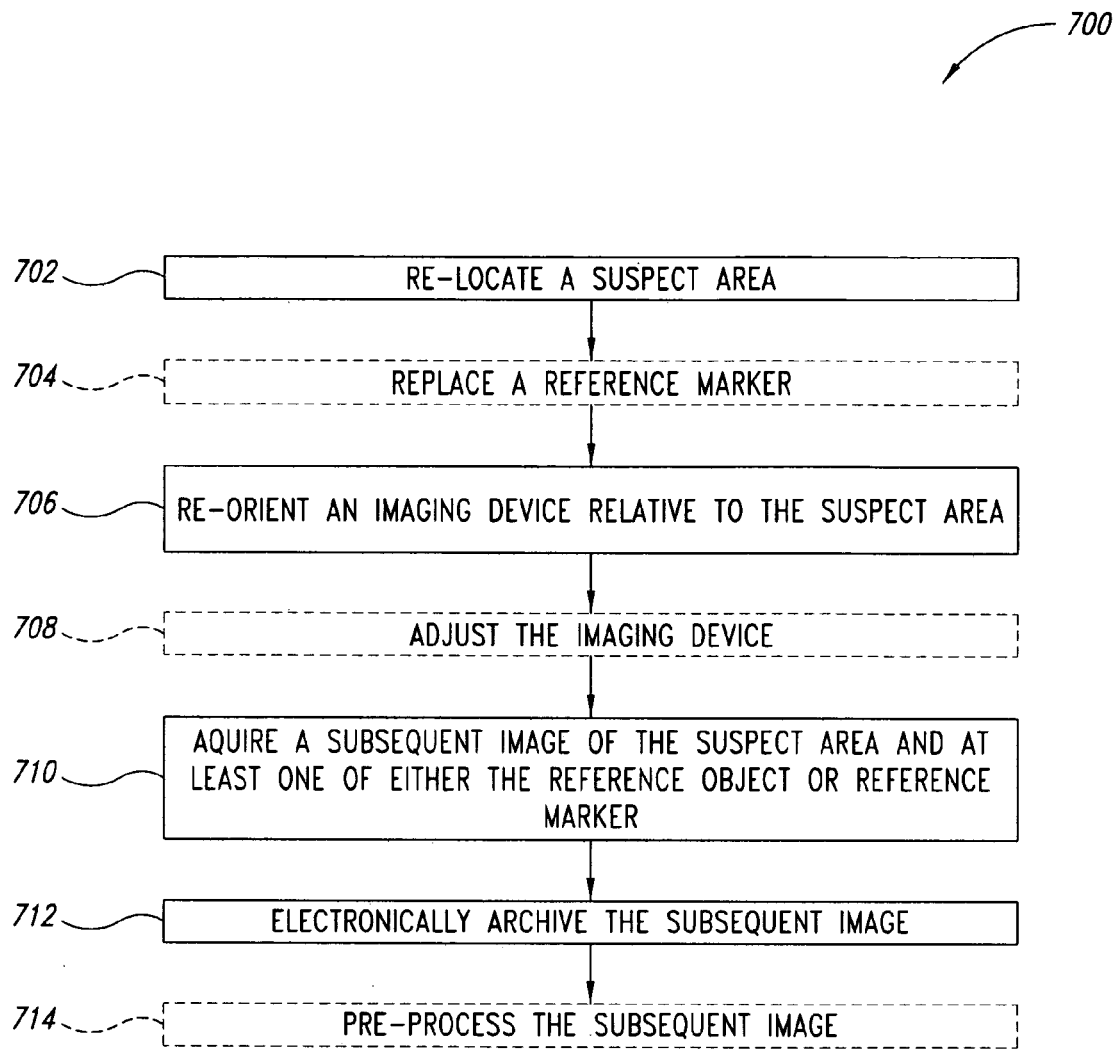
FIG. 7 is a flowchart of a method of acquiring a subsequent image of a suspect area according to one illustrated embodiment.

FIG. 7 shows a method 700 of acquiring a subsequent image of the suspect area 302 according to one embodiment. Method 700 differs from the previous method 400 in that method 700 includes relocating the suspect area 302 and realigning the imaging device 10, 100, 200. At 702, the suspect area 302 is relocated on the patient. As explained above, one of the purposes of the embodiments described herein is to track the changes of a suspect area 302. Because some patients may have many suspicious areas that are crowded together in one location or suspicious areas that rapidly change, it is important to relocate the exact area that is to be re-evaluated.

The suspect area 302 can be relocated by visually inspecting the patient, reviewing the patient's records, reviewing the position of a documented reference object and then measuring to obtain the position of the suspect area 302, automated by the computing system, or some combination thereof. At 704, a reference marker 318 can be repositioned on the patient proximate to the suspect area 302, if necessary.

The patient is positioned at 706 and an imaging device 10, 100, 200 is reoriented and/or realigned relative to the suspect area 302. Recall that a distance and an angle of the imaging device 10, 100, 200 used to acquire a subsequent image should be approximately matched to a distance and an angle of the imaging device 10, 100, 200 of a previous image. The orientation of the imaging device 10, 100, 200 does not have to exactly match because a transformation algorithm can be used to account for some amount of deviation in the angle, the distance, and even the lighting. At 708, a parameter (e.g., functional features such as zoom, contrast, etc.) on the imaging device 10, 100, 200 may be adjusted to enhance a quality of the image, if necessary.

At 710, a subsequent image is acquired that captures both the suspect area 302 and one of either the reference object 311 or the reference marker 318. At 712, the subsequent image is electronically archived according to the archiving process described above. Optionally, at 714, the subsequent image may be pre-processed as described above and illustrated in FIG. 6.

Image Transformation

Figure 8B:
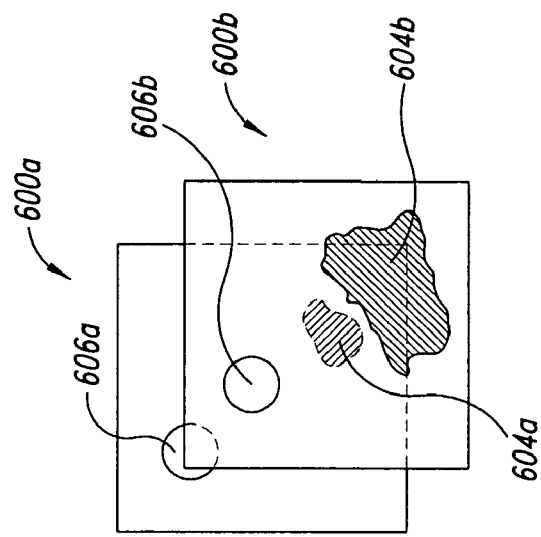
FIG. 8B is a top plan view of the first image and the second image of FIG. 8A transformed to have approximately the same respective orientation and size.
Figure 8A:
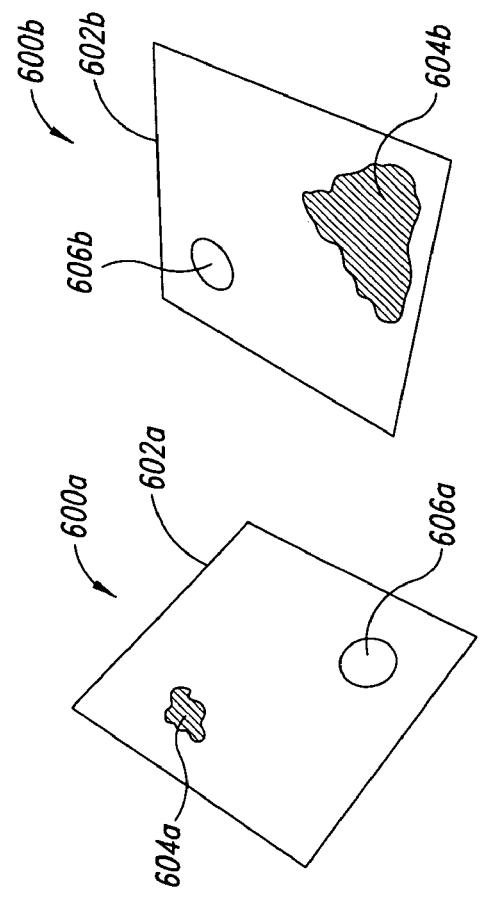
FIG. 8A is left, front isometric view of a first image and a second image, each having in an initial and respectively different orientation and size according to one illustrated embodiment.

FIG. 8A shows two images 600*a*, 600*b* undergoing a transformation according to one embodiment. A first image 600*a* includes a first frame 602*a* enclosing a first reference image 606*a* and a first image 604*a*. The orientation of the first frame 602*a* results from the angle and position of the imaging device 10, 100, 200 when the image was acquired. A second image 600*b* includes a second frame 602*b* enclosing a second reference image 606*b* and a second image 604*b*, wherein both the first image 604*a* and the second image 604*b* are images of the suspect area 302. It should be understood the second reference image 600*b* may be skewed, of a different size, or otherwise misaligned with respect to the first reference image 600*a*. Thus, the transformation algorithm is used to align, size, deskew, or otherwise manipulate the second reference image 606*b* to match the first reference image 606*a* as closely as possible. Moreover, any changes made to the second reference image 606*b* during the transformation process are made to the entire image 600*b* and everything enclosed within the image 606*b*. For example, if the reference image 606*b* is scaled down by ten percent, then the second frame 602*b*, the reference grid (not shown for clarity), and the second image 604*b* are also scaled down by ten percent. Further it should be noted that reference image 606*a* and 606*b* need not be separate from images 604*a* and 604*b*, but can be points within or on images 604*a* and 604*b* that are considered by the computer algorithm during the fit analysis.

FIG. 8B shows the same two images from FIG. 8A about to be overlaid after the second image 600*b* has been transformed. Once the images 600*a*, 600*b* are overlaid with respect to one another, a comparison algorithm can be employed to detect, map, and document differences, if any, between the first image 604*a* and the second image 604*b*.

Methods of Comparing Images

Figure 9:
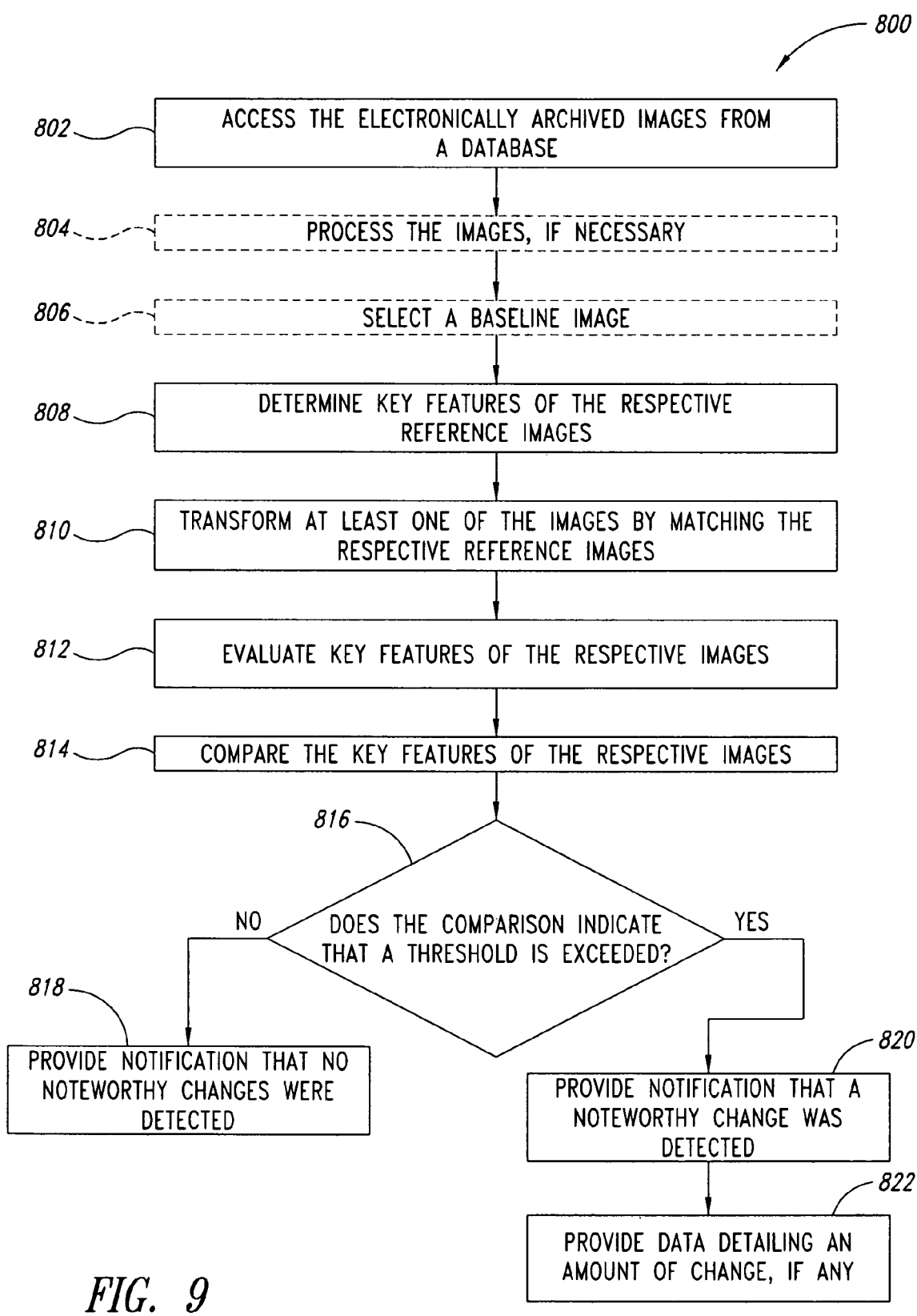
FIG. 9 is a flowchart of a method of comparing at least two images of a suspect area according to one illustrated embodiment.

FIG. 9 shows a method 800 to compare subsequent images 600*a*, 600*b* taken of a suspect area 302 according to one illustrated embodiment. This comparison can take place in a variety of settings, for example in the facility where the patient is treated or in a remote facility. The comparison, when done remotely, simply means that images of the suspect area 302 are forwarded to another location, which could be by a computer algorithm or a third party technician that specializes in performing the image comparisons. The images can be transferred to the remote facility through any available means, for example over a computer network (private or the Internet), through a file transfer protocol (FTP) system, by courier or regular mail, with the images stored on a computer readable medium such as a compact disk, magnetic storage device, or other equivalent digital storage media.

The method 800 can commence with the first image 600*a* being compared to a second, subsequent image 600*b*, for example. In the present embodiment, the images have been electronically archived, but they may not have been pre-processed. In addition, the present embodiment is not limited to the comparison of only two images. It is appreciated and understood that multiple images can be simultaneously compared against a baseline image and/or relative to each other. For example, each image taken over the preceding six months could be simultaneously compared to a first image 600*a* taken the previous year. In one embodiment, an animation software program can be used to animate the changes in the suspect area 302 over time. For purposes of clarity and brevity, however, the comparison of only two images will be described below.

At 802, the electronically archived images are accessed from a database of images. At 804, the images are pre-processed, if desired. Optionally, at 806 a user may select a baseline image 600*a*. The baseline image could be a first acquired image, an intermediately acquired image, or an image taken during the patient's previous office visit. For purposes of detecting changes, it is not necessary, but may be helpful to select a baseline image.

At 808, a mapping algorithm can be used to determine key features, such as a border or perimeter of the reference images 606*a*, 606*b*. Alternatively, a mapping algorithm may look for key points on the reference images 606*a*, 606*b* with respect to the reference grid 608 (FIG. 6) or may use reference images 606*a* and 606*b* as points on images 604*a* and 604*b* during the fit analysis. In all of the embodiments described herein reference images 606*a* and 606*b* should be understood to be an image such as a landmark feature on the surface or simply a reference point or pixel or collection of pixels either separated from images 604*a* and 604*b* or on or within 604*a* or 604*b*. Thus, the term image should be construed to mean a point that can be captured in a digital form and used as a reference point.

At 810, a transformation algorithm is used to transform the second image 600*b* into a comparative posture with the first image 600*a* by using the reference images 606*a*, 606*b*. In one embodiment, the reference image 600*b* is scaled up or down in size, rotated, skewed, or otherwise manipulated so that the reference images 606*b* is approximately the same size, same orientation, and in the same position within the frame 602*b* as the first reference image 606*a* of frame 602*a*. In an alternate embodiment, both images 600*a*, 600*b* can be scaled up or down in size, rotated, skewed, or otherwise manipulated so that the respective reference images 606*a*, 606*b* are approximately the same size, have the same orientation, and are in the same position with respect to the reference grid 608 (FIG. 6). It should be understood that in certain aspects the reference images 606*a* and 606*b* are in fact contained within images 604*a* and 604*b*. Such reference images may correspond to points on the perimeter of images 604*a* and 604*b* that appear unchanged once the images are sized and overlaid. As one of ordinary skill in the art can readily appreciate the more reference points taken into account during the fit analysis, the higher the quality of the comparison. Accordingly, in certain embodiments at least two reference points are considered, in other embodiments, at least 3, 4, 5, 6, 7, 8, 9, 10, 15, 20, or more are utilized by the algorithm.

At 812, after the reference images 606a, 606b have been sufficiently matched during the transformation process; a comparison algorithm is used to evaluate and compare the respective images 604a, 604b. Key points or parameters are identified in both the first image 604a and the second image 604b. For example, the overall area, the perimeter or border length, the percentage change in size in a given quadrant, etc. are just some of the parameters that can be evaluated in each respective image 604a, 604b.

In addition, a color, contrast, and/or a depth of each of the respective images 604a, 604b can be determined. Balancing the color, brightness, and/or the contrast of the respective images is described below. The features that are to be evaluated can be selected by a user or can be selected automatically.

At 814, the images 604a, 604b are compared with respect to one another to identify differences between the evaluated features. For example, the areas or perimeter lengths of the respective images 604a, 604b can be compared. The differences may be subtle, like slight changes in color or they may be substantial like a greatly enlarged area of the second image 604b.

At 816, any identified differences are further compared to determine if a threshold is exceeded. For example, the threshold could be one, two, three, four, five, six, seven, eight, nine, ten, fifteen, twenty, twenty-five percent increase in the area of the second image 604b compared to the area of the first image 604a. At 818, if there are no detected differences or if the detected differences do not exceed the threshold, then a notification is provided that no noteworthy changes of the image 604b were detected. At 820, if the detected differences do exceed the threshold, then a notification is provided that noteworthy changes of the image 604b were detected. The threshold can be a user defined setting, a preprogrammed setting, or an automatically adjustable range depending on the image quality and resolution, for example.

At 822, data is provided detailing the specific changes, for example, shape, color, texture, a shift in position, etc. The data and/or the results obtained from the comparison can be made available to the medical professional in a short amount of time to enable the medical professional to make a more objective, informed diagnosis and to quickly formulate a treatment plan. Additionally or alternatively, a post-processing algorithm can be used to overlay the respective images 600a, 600b on a screen. Color-coding, animation techniques, and other graphic processing techniques can be used to identify areas or regions of greatest change.

In certain embodiments, images may be captured and compared using only a standard imaging device, which includes, digital cameras, movie cameras, film cameras etc., as long as the image to be compared is at some point moved to a digital format thus allowing computational analysis thereon. Clearly in one embodiment an image from a standard consumer model digital camera is compared against a subsequent image. In such embodiments, the computer algorithm used will perform a best fit or transformation of the images by modifying size, angle, and brightness, to obtain the best possible fit prior to analysis for changes. Accordingly, in such embodiments users already having an archive of older images can compare these images. While the error rate for such comparison is slightly higher, the flexibility of being able to review older images far exceeds the risk of a few false positive outcomes that can be easily discounted by the user upon further review. It should also be clearly understood that images taken with no focal length limiter, brightness, color, or contrast control can be compared with images having such controls.

Color and/or Contrast Balancing to Detect a Suspect Area

Figure 10A:
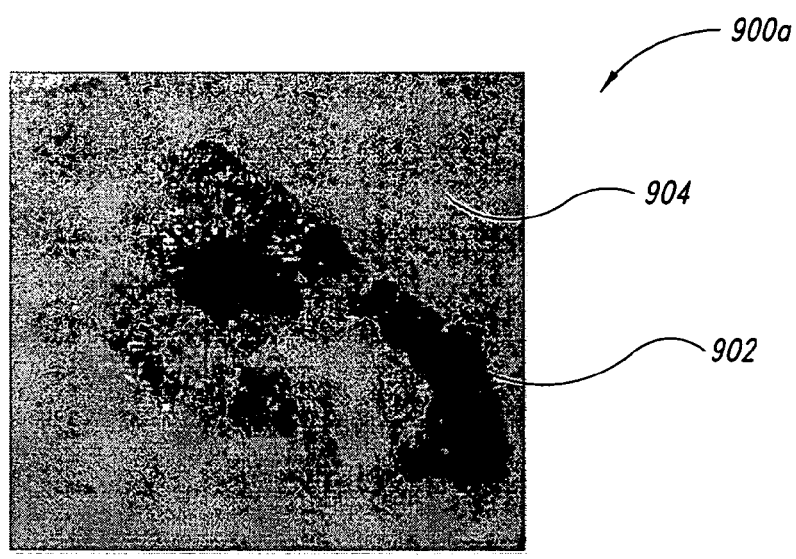
FIGS. 10A-10C are images of suspect areas illustrating the various stages of the color balancing method of FIG. 11 according to one illustrated embodiment.
Figure 10B:
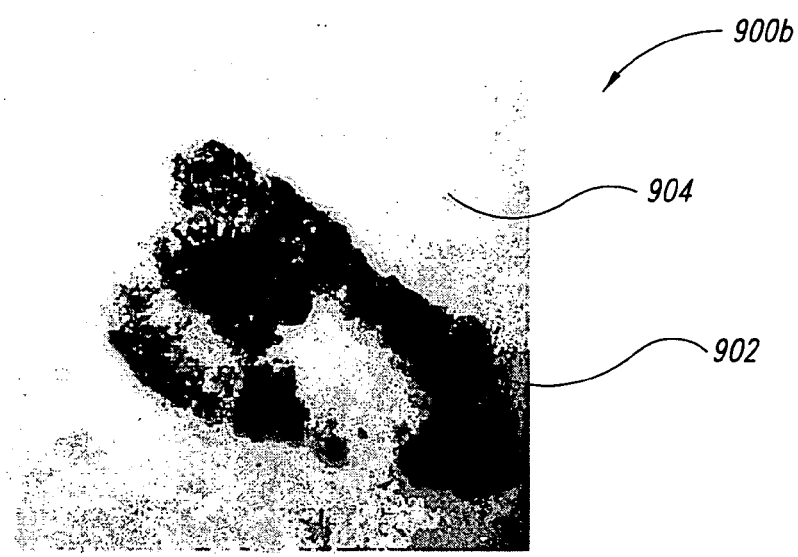
Figure 10C:
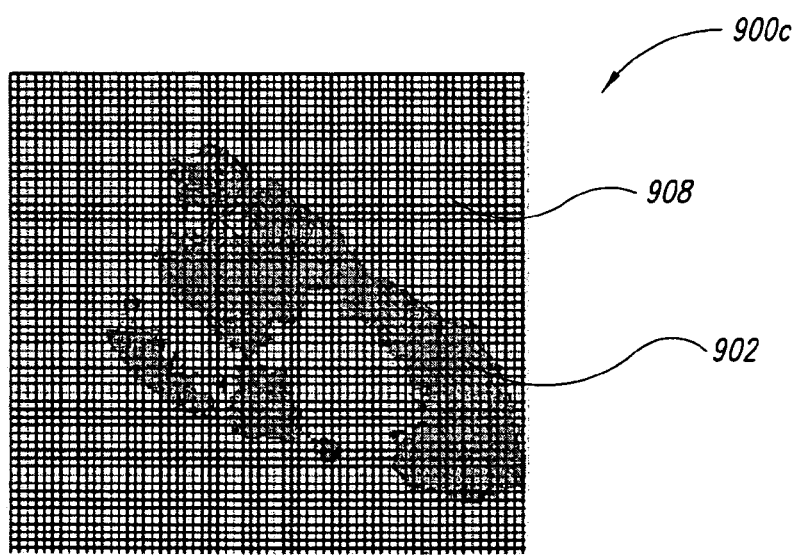

FIGS. 10A, 10B, and 10C illustrate the color balancing of an image 900. In particular, FIG. 10A shows a digital image 900a of a suspect area 902 and a background region 904 prior to color balancing. FIG. 10B shows the image 900b after a filter has been applied to filter out the background skin region 904 based on the color, brightness, and/or contrast of the suspect area 902 compared to the background skin region 904. FIG. 10C shows the image 900c after it has been pre-processed, which may include but is not limited the application of additional filters to remove other features in the image and/or the application of a reference grid 908 over the image 900c.

Due to slight differences in lighting and environment, the colors in an image will likely not be constant from one image to the next, even though steps are taken to provide constant lighting. Moreover, a skin does not provide an adequate background for evaluating color changes of a suspect area because the skin can change color, for example the skin may be darker in the summer than in the winter.

One advantage of color balancing is to provide an additional parameter that can be compared from one image to the next, for instance the respective darkness or lightness of the respective images. A second advantage of color balancing permits a comparison between the suspect area and the surrounding skin as a means to more accurately detect suspect areas 302 over a larger skin surface.

Figure 11:
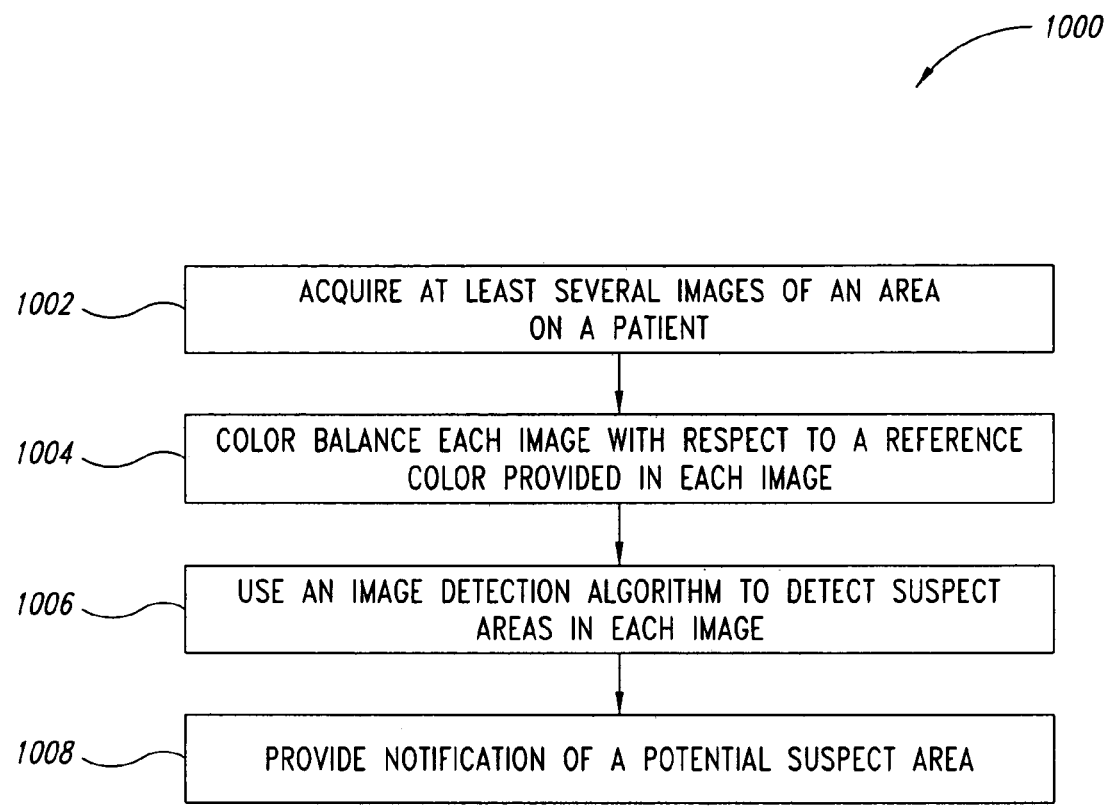
FIG. 11 is a flowchart of a method of color balancing an image to detect a potential suspect area according to one illustrated embodiment.

FIG. 11 shows a method 1000 of detecting suspect areas over a surface of skin 14 by means of image filtration (i.e., color or contrast balancing). At 1002, at least several images over a large area of skin are acquired. The images may have overlapping sections to insure that the entire skin area was imaged. In addition, reference markers 318 can be placed at various locations on the imaged skin area so that any potential suspect areas 302 that may be discovered can be relocated at a later time.

At 1004 and according to one embodiment, each image is color balanced with respect to a reference color. In one embodiment, the reference color appears in the acquired image. Such a reference could include distance measurements, contrast standards, color standards, etc. The reference color can be a color palette of single color placed within the frame of the image when the image is acquired (FIG. 2A). The color palette can have a variety of shades or colors thereon. Because the reference colors are electronically isolatable, the color and/or shading of the image can be digitally adjusted until a feature in the image approximately matches a certain reference color.

At 1006, after the color of the image has been adjusted, a spot detection algorithm is used to process each of the respective images to detect any suspect areas 302 in one or more images. In one embodiment, a filter is applied to the image to make darker objects, such as a mole, stand out relative to the skin. The type of filter used will depend on the amount of color contrast between the skin and the suspect area. By way of example, images of a light skinned person with dark patches on their skin may not require filtering; whereas images of a dark skinned person with moderately dark patches on their skin may require a series of filters to achieve enough contrast between the skin and the suspect area.

In 1008, notification of a potential suspect areas is provided to the medical professional. At this point, the medical professional could perform a refined evaluation of any potential suspect area by taking higher resolution images of the suspect area and comparing these images over time, as described in detail above. Additionally or alternatively, the medical professional can perform or recommend that a biopsy be taken of the suspect area.

Computing Systems

The computing system for performing the image comparisons may include a number of local computers for receiving downloaded images and at least one mainframe computer for performing the image comparisons. Alternatively, the image comparisons could be performed on the local computers.

The local computer typically includes a processor, memory, multiplex ("Mux") card, video and Ethernet cards, power supply and an image acquisition card. A number of local computers be networked together and service a number of patient treatment facilities. The local computer can communicate with other local computers and/or the mainframe computer over a communications link such as a local area network ("LAN") and/or a wide area network ("WAN"). The communications link can be wired and/or wireless. The communications link can employ Internet, or World Wide Web communications protocols, and can take the form of a proprietary extranet. In such instances a user could obtain images and upload these to a web-based server that could perform all the analysis and send back to the user only the analysis or only the analysis that yielded possible changes. In other embodiments all algorithms could reside on the computer wherein the images or uploaded or on a server directly connected thereto. In certain embodiments, patient confidentiality is maintained.

In certain specific embodiments a user could upload all patient information into a database and also have image analysis linked thereto. Accordingly, either on a remote server or housed in the users facility could be a computer that contains a database with a unique patient identifier, this identifier can be used to add new images to a patient folder and the image analysis could either be performed immediately while the user waits or could be performed in the background. Subsequent to this analysis a notification could be sent via email or secured web-access or the like that indicates the analysis has been completed and either no action is necessary or further review/action may be required, thus indicating a change was noted between the images.

The various embodiments described above can be combined to provide further embodiments. All of the above U.S. patents, patent applications and publications referred to in this specification are incorporated herein by reference. Aspects can be modified, if necessary, to employ devices, features, and concepts of the various patents, applications and publications to provide yet further embodiments.

These and other changes can be made in light of the above detailed description. In general, the terms used in the claims should not be construed to limit the claims to the specific embodiments disclosed in the specification and the claims, but should be construed to cover all imaging devices, types of image formats, measuring techniques, and image transformation and comparison algorithms. Accordingly, the claims are not limited by the disclosure.

What is claimed is:

1. A method of comparing at least two images of a suspect area of a patient, the method comprising:
   providing at least two images of the suspect area;
   digitally overlaying the at least two images;
   performing a best-fit transformation of one image using a stored transformation algorithm to encourage the one image to approximately correspond to at least one detected attribute of the other acquired image;
   comparing the at least two images to determine whether a difference exists between an aspect of the one image when compared with the same aspect of the other image; and
   wherein subsequent to comparing the at least two images, a computer algorithm provides an output that describes the presence or absence of the difference between the at least two images.

2. The method of claim 1, further comprising:
   determining whether a correlation between the at least two images permits the at least two images to be digitally compared.

3. The method of claim 1 wherein the detected attribute is a perimeter of the suspect area.

4. The method of claim 1 wherein the detected attribute is a two dimensional surface area of the suspect area.

5. The method of claim 1 wherein comparing the at least two image to determine whether the difference exists between the aspect of the one image when compared with the same aspect of the other image includes determining if a change between the respective aspects exceeds a threshold.

6. The method of claim 5, further comprising:
   providing an indication that the threshold is exceeded.

7. The method of claim 1, further comprising performing at least one of the best-fit transformation and the comparison of the at least two images without any significant human intervention.

8. The method of claim 7, further comprising performing the best-fit transformation and the comparison of the at least two images using algorithms for a computing system.

9. The method of claim 1, further comprising comparing the at least two images using a comparison algorithm on a computer readable memory of a computing system.

10. The method of claim 1, wherein performing the best-fit transformation includes processing substantially all of the suspect area in the at least two images.

11. A method for monitoring a dermal area of a patient comprising:
    providing at least a first and second image of the dermal area;
    digitally overlaying the at least first and second image;
    performing a best-fit transformation of one image using a transformation algorithm to encourage the one image to approximately correspond to at least one detected attribute of the other acquired image;
    comparing the at least two images to determine whether a difference exists between an aspect of the one image when compared with the same aspect of the other image; and
    wherein subsequent to comparing the at least two images, a computer algorithm provides an output that describes the presence or absence of the difference between the at least two images.

12. The method of claim 11, wherein said dermal area of a patient is at risk of developing a melanoma.

13. A system to acquire an image of a suspect area of a patient, the system comprising:
    means for acquiring at least two images of the suspect area;
    means for digitally overlaying the suspect area captured in one of the at least two images and the suspect area captured in the other one of the at least two images;

means for performing a best-fit transformation to encourage the one acquired image to approximately correspond to at least one detected attribute of the other acquired image; and means for detecting whether a difference exists between an aspect of the transformed one acquired image when compared with the same aspect of the other acquired image, wherein a computer algorithm provides an output that describes the presence or absence of the difference between the at least two images.

14. The system of claim 13 wherein the means for comparing the two images comprises instructions on a computer readable memory and executable by a computing system, the instructions operable to cause the computing system to perform a best-fit transformation of the one acquired image relative to the other acquired image.

15. The system of claim 13 wherein the means for detecting includes instructions on a computer readable memory and executable by a computing system, the instructions operable to cause the computing system to select a threshold value to indicate whether the difference between the aspect of the one acquired image when compared with the sane aspect of the other acquired image warrants additional attention.

16. A method of analyzing a suspect area of a patient, the method comprising:

transforming a captured first image of the suspect area using a best-fit transformation algorithm performed by a computing system to encourage the first image to approximately fit to a captured second image;

comparing the transformed first image and the second image using a comparison algorithm of the computing system; and outputting information based on the comparison of the transformed first image and the second image, wherein a computer algorithm provides the outputted information that describes the presence or absence of the difference between the first image and the second image.

17. The method of claim 16, wherein performing the transformation of the captured first image, the comparison of the transformed first image and the second image, and the outputting of information are automatically performed by the computing system without any significant human intervention.

18. The method of claim 16, wherein the transformed first image and the second image are overlayed by the computing system.

19. The method of claim 16, wherein the computing system executes transformation instructions operable to resize, skew, color balance, and adjust brightness of the first image.

* * * * *

UNITED STATES PATENT AND TRADEMARK OFFICE
CERTIFICATE OF CORRECTION

| | | |
|---|---|---|
| PATENT NO. | : 7,657,101 B2 | Page 1 of 1 |
| APPLICATION NO. | : 11/336649 | |
| DATED | : February 2, 2010 | |
| INVENTOR(S) | : William T. Christiansen, II et al. | |

It is certified that error appears in the above-identified patent and that said Letters Patent is hereby corrected as shown below:

Column 18
Line 22, "two image to determine whether the difference exists between" should read --two images to determine whether the difference exists between--.

Column 19
Line 22, "acquired image when compared with the sane aspect of the" should read --acquired image when compared with the same aspect of the--.

Column 20
Line 23, "executes transformation instructions operable to resize, skew," should read --executes best-fit transformation instructions operable to resize, skew,--.

Signed and Sealed this

Fifteenth Day of June, 2010

David J. Kappos
*Director of the United States Patent and Trademark Office*

UNITED STATES PATENT AND TRADEMARK OFFICE
CERTIFICATE OF CORRECTION

PATENT NO.       : 7,657,101 B2                    Page 1 of 1
APPLICATION NO. : 11/336649
DATED            : February 2, 2010
INVENTOR(S)      : Christiansen, II et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 617 days.

Signed and Sealed this

Twenty-eighth Day of December, 2010

David J. Kappos
*Director of the United States Patent and Trademark Office*